United States Patent [19]

Schmand

[11] Patent Number: 5,093,529

[45] Date of Patent: Mar. 3, 1992

[54] PROCESS FOR THE PREPARATION OF FLUORINATED BENZOIC ACIDS

[75] Inventor: Horst Schmand, Bad Nenndorf, Fed. Rep. of Germany

[73] Assignee: Cassella Aktiengesellschaft, Frankfurt am Main, Fed. Rep. of Germany

[21] Appl. No.: 553,262

[22] Filed: Jul. 16, 1990

[30] Foreign Application Priority Data

Jul. 28, 1989 [DE] Fed. Rep. of Germany ....... 3925036
Apr. 30, 1990 [EP] European Pat. Off. ......... 90108226.3

[51] Int. Cl.$^5$ ............................................. C07C 45/00
[52] U.S. Cl. .................................... 568/323; 562/493; 568/308
[58] Field of Search ......................... 562/493; 568/323

[56] References Cited

FOREIGN PATENT DOCUMENTS 3529259 2/1987 Fed. Rep. of Germany.

OTHER PUBLICATIONS

Chemical Abstract of "The Synthesis of β-Receptor Blocking Substances", vol. 85, No. 15, 11, Oct. 1976, p. 436.

Primary Examiner—Paul J. Killos
Attorney, Agent, or Firm—Connolly and Hutz

[57] ABSTRACT

In the process for the preparation of fluorinated benzoic acids of the formula I

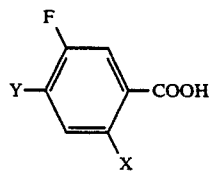

in which X and Y, for example, independently of one another denote chlorine or fluorine and X moreover denotes bromine, a fluorinated chloroacetophenone of the formula II

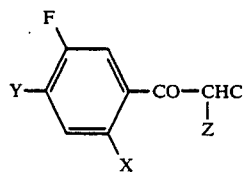

in which Z denotes chlorine or hydrogen, is reacted with a hypohalite.

6 Claims, No Drawings

PROCESS FOR THE PREPARATION OF FLUORINATED BENZOIC ACIDS

The invention relates to a process for the preparation of fluorinated benzoic acids of the formula I

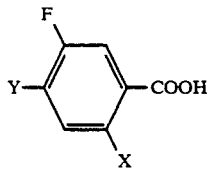

in which
X denotes Br, Cl or F,
Y denotes Cl or F and
one of the radicals X or Y also denotes hydrogen.

The compounds of the formula I are known and are employed, for example, as intermediates for the preparation of antibacterial 6-fluoroquinolonecarboxylic acids (compare EP-A2-303,291, page 5, lines 25 et seq., and EP-A2-342,849, page 10, lines 30 et seq.).

According to the process disclosed in EP-A2-303,291, 2-chloro-4,5-difluorobenzoic acid is prepared by acylating 1-chloro-3,4-difluorobenzene to give 2-chloro-4,5-difluoroacetophenone with a yield of 82% of theory and then oxidizing with sodium hypochlorite to 2-chloro-4,5-difluorobenzoic acid in a yield of 85.1% of theory. The total yield of this process thus only amounts to about 70% of theory, relative to the 1-chloro-3,4-difluorobenzene as the starting material. It is further a disadvantage of this process that, according to the illustrative example, the acylation must be carried out at a temperature of 120° C.

According to the process of unexamined Japanese Patent Publication No. 108,839/1987, 2-chloro-4,5-difluorobenzoic acid is prepared from 2-chloro-4,5-difluorobenzotrifluoride, and 2,4,5-trifluorobenzoic acid is prepared from 2,4,5-trifluorobenzotrifluoride by reaction with sulphuric acid at temperatures of 100° to 140° C. A disadvantage of this process if the liberation of hydrogen fluoride at temperatures above 100° C., as a result of which special reactor materials become necessary.

In Example 14 of EP-A2-342,849, 1-bromo-3,4-difluorobenzene is reacted at 120° C. with acetyl chloride and aluminium chloride (molar ratio:1:1.5:2.5) for 2 hours. Excess reagents and the Friedel-Crafts complex are hydrolysed in ice and the reaction product 2-bromo-4,5-difluoroacetophenone is then reacted with methylene chloride. After evaporating off the methylene chloride, the 2-bromo-4,5-difluoroacetophenone is oxidized to the acid with excess industrial bleaching liquor (sodium hypochlorite solution) by heating to reflux for 2 hours. After customary working up and a reprecipitation, 2-bromo-4,5-difluorobenzoic acid is obtained in a yield of 50% of theory. Because of the impurities present, the melting point is only 102° to 104° C.

The object of the present invention is to indicate a process for the preparation of compounds of the formula I which does not have the disadvantages of the previous processes. In particular, the process according to the invention is to yield the compounds of the formula I under milder conditions, more economically and in high yields and purities.

It has surprisingly been found that fluorinated chloroacetophenones of the formula II

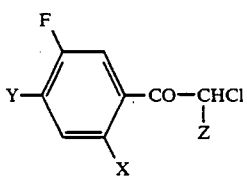

in which
X denotes Br, Cl or F,
Y denotes Cl or F,
Z denotes H or Cl and
one of the radicals X or Y also denotes hydrogen,
can be prepared in excellent yields by reaction of compounds of the formula III

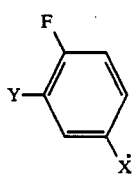

in which
X denotes Br, Cl or F,
Y denotes Cl or F
and one of the radicals X or Y also denotes hydrogen, with mono- or dichloroacetyl chloride at temperatures of 20° to 100° C. and can then be reacted with a hypohalite to give the fluorinated benzoic acids of the formula I in excellent yields.

The invention therefore relates to a process for the preparation of trifluorinated benzoic acids of the formula I

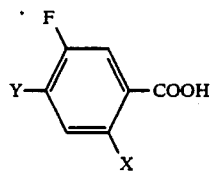

in which
denotes Br, Cl or F,
Y denotes Cl or F
and one of the radicals X or Y also denotes hydrogen, and is characterized in that a fluorinated chloroacetophenone of the formula II

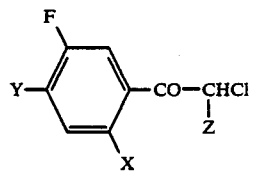

in which
X denotes Br, Cl or F,
Y denotes Cl or F,
Z denotes H or Cl and
one of the radicals X or Y also denotes hydrogen, is reacted with a hypohalite. In this reaction, the compound II is oxidized to the corresponding carboxylic acid I.

In the formulae I, II and III Y preferably denotes fluorine and X preferably denotes fluorine or chlorine, and in the formula II Z moreover preferably denotes chlorine.

The hypohalite may be, for example, an alkaline earth metal hypohalite, such as, for example, calcium hypochlorite, or in particular an alkali metal hypohalite, for example an alkali metal hypobromite or alkali metal hypochlorite. Preferred hypohalites are the hypochlorites and, in particular, hypobromites. Other examples of suitable hypohalites are: potassium hypochlorite and sodium hypochlorite (for example also in the form of the so-called bleach liquor or chlorine bleaching liquor), potassium hypobromite and sodium hypobromite, of which sodium hypobromite is preferred.

The hypohalite may also be generated in situ from the halogen, in particular chlorine or bromine, and an aqueous solution of an alkaline earth metal hydroxide or alkali metal hydroxide, in particular potassium hydroxide solution or sodium hydroxide solution. A mixture of a hypohalide with an alkaline earth metal hydroxide and/or alkali metal hydroxide and/or a mixture of different hypohalites may also be employed as the hypohalite.

The oxidation of the fluorinated chloroacetophenones of the formula II with the hypohalite is expediently carried out in the aqueous phase and at temperatures of 0° to 100° C., preferably 10° to 80° C. and very particularly preferably 20° to 60° C. Preferably, in this case an aqueous solution of the hypohalite is initially introduced and the compound of the formula II is added, in particular added dropwise or metered in. It is expedient for the conversion of 1 mole of α,α-dichloroacetophenone of the formula II (Z in this case denotes chlorine in formula II) into the compounds of the formula I to employ at least 2 moles of hypohalite. For the conversion of 1 mole of chloroacetophenone of the formula II (Z in this case denotes hydrogen in formula II), at least 3 moles of hypohalite are expediently employed. If an excess of hypohalite over the minimum amounts mentioned is necessary at all for carrying out the process according to the invention in practice, in the main only a minimum excess is required.

When using a hypochlorite, for example sodium hypochlorite, in some cases a larger excess is required than when using a hypobromite, for example sodium hypobromite. Of course, the use of a larger excess of hypohalite is usually possible, but is not necessary or is not expedient for economic reasons.

The compounds of the formula I can be isolated from the reaction mixture in a customary manner, for example by precipitating with a mineral acid, such as, for example, hydrochloric acid. For the precipitation of the compounds of the formula I with a mineral acid, it is expedient, for example in the use of hypobromite as an oxidizing agent, to add a disulphite, for example sodium disulphite ($Na_2S_2O_5$) in order to prevent discolourations which may otherwise occur with the liberation of bromine owing to reaction of excess hypobromite with the acid.

The fluorinated chloroacetophenones (α-chloroacetophenones and α,α-dichloroacetophenones) of the formula II are novel and are claimed in the context of the present invention. Preferred compounds of the formula II are those in which Y denotes fluorine and X denotes fluorine or chlorine and Z denotes hydrogen or, in particular, chlorine. The compounds of the formula II are obtained in excellent yields by reacting a compound of the formula III

in which
X denotes Br, Cl or F,
Y denotes Cl or F
Y denotes Cl or F
and one of the radicals X or Y also denotes hydrogen and, preferably, Y denotes fluorine and X denotes fluorine or chlorine, with mono- or dichloroacetyl chloride in the presence of an acylating catalyst. The reaction with monochloroacetyl chloride yields the compounds of the formula II where Z=hydrogen, and the reaction with dichloroacetyl chloride yields the compounds of the formula II where Z=chlorine, in each case in excellent yields. In both cases, the reaction can normally be carried out at a temperature of 20° to 100° C. The use of temperatures above 100° C. is not necessary. The reaction is preferably carried out at a temperature of 20° to 90° C. and very particularly preferably at 20° to 80° C. Temperatures of 20° to 70° C. can usually be used for the reaction of the compounds of the formula III with dichloroacetyl chloride. The reaction can also be carried out in an inert diluent, thus, for example, in nitrobenzene or a halohydrocarbon, such as, for example, dichloroethane or trichlorethane, or in a mixture of inert diluents. However, the reaction is preferably carried out without diluents.

Suitable acylating catalysts are Lewis acids, such as, for example, aluminium chloride, aluminium bromide, zinc chloride, boron trifluoride, iron(III) chloride, tin(IV) chloride, titanium tetrachloride and other so-called Friedel-Crafts catalysts. Aluminium chloride is customarily used. The acylating catalysts mentioned are employed, as is customary, in anhydrous form.

The fluorobenzenes of the formula III are known or can be prepared by methods which are known per se. Mono- and dichloroacetyl chloride are known compounds. Expediently, fluorobenzene of the formula I, mono- or dichloroacetyl chloride and acylating catalyst in a molar ratio 1:(1 to 2):(1.2 to 3), preferably 1:(1 to 1.6):(1.3 to 2.5), are employed for the reaction. When using dichloroacetyl chloride, the molar ratio fluorobenzene of the formula I: dichloroacetyl chloride: acylating catalyst is in many cases : (1.1 to 1.6):(1.3 to 2.1).

The compounds of the formula II are obtained in excellent yields of customarily 89% of theory and more under mild conditions and can as a rule be employed without further purification in the subsequent oxidation with hypohalite. The reaction according to the invention of 1,2,4-trifluorobenzene with chloroacetyl chloride to give 2,4,5-trifluoro-α-chloroacetophenone proceeds even at moderate temperatures in yields of 89 to 90% of theory. Yields of 95% of theory and more are obtained even at mild temperatures in the reaction according to the invention of 1-chloro-3,4-difluorobenzene with chloroacetyl chloride to give 2-chloro-4,5-difluoro-α-chloroacetophenone. This was highly surprising since, for example, in the reaction of 1-chloro- 3,4-difluorobenzene with acetyl chloride under comparable conditions, 2-chloro-4,5-difluoroacetophenone can only be obtained in substantially lower yields and 1,2,4-trifluorobenzene does not react with trichloroacetyl chloride at all under comparable conditions to give the desired α,α,α-trichloroacetophenone.

Through the use of dichloroacetyl chloride, which is preferred, not only can the temperature necessary when using acetyl chloride for the reaction of similar fluorobenzenes of the formula I be considerably reduced in some cases, but moreover often only lower excesses of acylating agent and/or acylating catalyst are also necessary. Thus, in the process of EP-A2-303,291, 1-chloro-3,4-difluorobenzene is reacted with acetyl chloride in the presence of aluminium chloride in a molar ratio of 1:1.5:1.5, while according to the present invention 1-chloro-3,4-difluorobenzene can be reacted with dichloroacetyl chloride in the presence of aluminium chloride in a molar ratio of 1:1.2:1.5 compare Example 6 below), which denotes a reduction in the amount of acylating agent of 20%.

In the process of EP-A2-342,849, 1-bromo-3,4-difluorobenzene is reacted with acetyl chloride in the presence of aluminium chloride in a molar ratio of 1:1.5:2.5, while according to the process of the present invention 1-bromo-3,4-difluorobenzene is reacted with dichloroacetyl chloride in the presence of aluminium chloride in a molar ratio of 1:1.5:2.0 (compare Example 11 below), which denotes a reduction in the amount of the acylating catalyst of 20%.

Starting from compounds of the formula III, it is possible by means of the present invention to prepare fluorinated benzoic acids of the formula I in excellent yields and purities without temperatures above 100° C. having to be used in the course of the entire process. The process according to the invention furthermore has, for example, the advantage that at least one oxidation equivalent has already been incorporated in the side chain of the compound of the formula II, so that the hypohalite oxidation can be carried out in a milder manner and using less hypohalite than was hitherto possible in comparable cases.

In a subsequent reaction with hypohalite of the compounds of the formula II obtained, yields of the fluorinated benzoic acids of the formula I are obtained which, relative to the fluorobenzene of the formula I employed, are normally 80% of theory and above.

The invention is further illustrated in the examples below. If not stated otherwise, percentage data relate to percentage by weight. The aluminium chloride used is employed in anhydrous form. The $^1$H— and $^{19}$F—NRM spectra were recorded using a 60 MHz instrument.

EXAMPLE 1

2,4,5-Trifluoro-α-chloroacetophenone 239 g (179 mol) of aluminium chloride are introduced into 99 g (0.75 mol) of 1,2,4-trifluorobenzene at 20° C. 130 g of chloroacetyl chloride (1.15 mol) are metered into the suspension at 60° C. with stirring in the course of 2 hours. The mixture is allowed to react further at 80° C. for 1 h and the liquid reaction product is then poured into 1 l of ice-water. The reaction product is extracted from the aqueous phase 3 times using a total of 300 ml of dichloromethane. The combined organic phases are dried over magnesium oxide and evaporated. The solid crude product is then distilled through a Vigreux column (b.p.: 104° C., 20 mbar).

139 g of solid 2,4,5-trifluoro-α-chloroacetophenone are obtained, which corresponds to 89% of theory, relative to 1,2,4-trifluorobenzene.

M.p.: 71°–73° C.

GC: 98.5%.

IR: 1704 cm$^{-1}$ ($>$C=O).

GC/MS: molar mass peak M$^+$: m/e 208 (principal product)

M$^+$—ClCH$_2$—CO=m/e 159.

M$^+$—(ClCH$_2$—CO)=m/e 131.

$^1$H—NMR (CDCl$_3$) δ ppn, relative to TMS: 6.9—7.4 ppm (1 H, m) 7.7–8.1 ppm (1 H, m) 4.6–4.8 ppm (2 H, s split).

F—NRM (CDCl$_3$) δ ppm, relative to C$_6$F$_6$: $-$21.8 to $-$22.8 ppm (1 F, m) $-$38.9 to $-$39.8 ppm (1 F, m) $-$53 to $-$54 ppm (1F,m).

EXAMPLE 2

2,4,5-Trifluorobenzoic acid 62.6 g (0.3 mol) of molten 2,4,5-trifluoro-α-chloroacetophenone, prepared according to Example 1, are added dropwise at 30° C. with stirring in the course of 2 to 846 g of sodium hypobromite solution (12.7% strength in NaOBr). The mixture is subsequently stirred at 30° C. for 30 min and then at 50° C. for 2 h.

After separating off the organic phase, the almost colourless aqueous is brought to pH 1 at 50° C. with the addition of sodium disulphite using 130 ml of hydrochloric acid.

In this manner, 48.0 g of 2,4,5-trifluorobenzoic acid are obtained, which is 81.0% of theory, relative to 1,2,4-trifulorobenzene, taking into account the acylation yield from Example 1. M.p.: 96°–98° C.

EXAMPLE 3

2-Chloro-4,5-difluoro-α-chloroacetophenone 50.8 g (0.45 mol) of chloroacetyl chloride are added dropwise at 65° C. in the course of 2½ h to 45.4 g (0.3 mol) of 1 chloro-3,4-difluorobenzene and 97.5 g (0.73 mol) of aluminium chloride. The mixture is then stirred at 65° C. for 1 and at 80° C. for a further 1½ h. The mixture is poured at about 70° C. into 625 g of ice-water. The phases are separated at room temperature and the organic phase is washed with 50 ml (2×25 ml) of water. After the separation, 65.8 g of liquid product are obtained, which corresponds to 95.7% of theory.

(GC purity: 96%). B.p.: 120°–123° C. (14.67 mbar).

IR: 1700 cm$^{-1}$ (C=O).

GC/MS: molar mass peak M$^+$: m/e 224 (principal product), M$^+$—ClCH$_2$=m/e 175 base peak, M$^+$—(ClCH$_2$—CO)=m/e 147.

$^1$H—NMR (CDCl$_3$) δ ppm, relative to TMS: 4.8 ppm (2 H, s), 7.25–7.75 ppm (2 H, m).

$^{19}$F—NMR (CDCl$_3$) δ ppm, relative to C$_6$F$_6$: $-$24.7 to $-$25.8 ppm (1 F, m), $-$33.4 to $-$34.4 ppm (1 F, m).

EXAMPLE 4

2-Chloro-4,5-difluorobenzoic acid 67.5 g (0.3 mol) of 2-chloro-4,5-difluoro-α-chloroacetophenone (prepared according to Example 3) are added dropwise at 30° C. and with stirring in the course of 1½ h to 846 g of sodium hypobromite solution (12.7% strength in NaOBr). The mixture is subsequently stirred at 30° C. for 30 min and then at 50° C. for 2 h.

After separating off the organic phase, the almost colourless aqueous phase is brought to pH 1 using 126 ml of hydrochloric acid at 50° C. with the addition of sodium disulphite.

In this manner 52.0 g of 2-chloro-4,5-difluorobenzoic acid are obtained, which is 86% of theory, relative to 1-chloro-3,4-difluorobenzene. M.p.: 103°–105° C.

EXAMPLE 5

3,4-Difluoro-α-chloroacetophenone 566 g (4.24 mol) of aluminium chloride are initially introduced with stirring into 228 g (2mol) of 1,2-difluorobenzene. 226 g (2 mol) of chloroacetyl chloride are added dropwise at 35° C. in the course of 2½ h. The mixture is subsequently stirred for 20 min and then warmed at 40° C. for 1 h. The mixture is then hydrolysed in 2000 g of ice-water. The organic phase is then separated off at 40° C. The organic phase becomes solid at room temperature and has a purity of 99% according to GC/MS.

The yield is 364 g of 3,4-difluoro-α-chloroacetophenone, which corresponds to 95.5% of theory, relative to 1,2-difluorobenzene.

GC/MS: Molar mass peak $M^{30}$: m/e 190, $M^+$—(ClCH$_2$)=m/e 141, $M^+$—(ClCH$_2$—CO)=m/e 113.

The 3,4-difluoro-α-chloroacetopheone can be reacted to give 3,4-difluoro-benzoic acid analogously to Examples 2 and 4.

EXAMPLE 6

2-Chloro-4,5-difluoro-α,α-dichloroacetophenone 100 g (0.75 mol) of anhydrous aluminium chloride are introduced in one portion at room temperature with stirring into 74.3 g (0.5 mol) of 1-chloro-3,4-difluorobenzene. The suspension is warmed to 65° C. and 89 g (0.6 mol) of dichloroacetyl chloride are added dropwise with the exclusion of moisture in the course of 3 h. The temperature is kept at 65° C. The mixture is subsequently allowed to react at 65° C. for 4 h and the olive-green liquid reaction mixture is then poured into 1 l of water for hydrolysis. The mixture is well stirred in the course of this, and the temperature is allowed to rise to about 60° C. The organic phase is separated off at about 50° C. in a separating funnel. 125 g of 2-chloro-4,5-difluoro-α,α-dichloroacetophenone are obtained, which corresponds to 96.4% of theory, relative to 1-chloro-3,4-difluorobenzene.

Purity (from GC/MS)=91%.

MS: Molar mass peak $M^{30}$=258 m/e (260 , $M^+$—CO—$^{35}$Cl=m/e 195, $M^{30}$—CHCl$_2$=m/e 175 base peak, $M^+$—(CHCl$_2$—CO)=m/e 147.

$^{19}$F—NMR (CDCl$_3$) δ ppm, relative to C$_6$F$_6$: −25.5 ppm to −26.6 ppm (1 F, m), −34.6 ppm to 35.6 ppm (1 F, m).

EXAMPLE 7

2-Chloro-4,5-difluorobenzoic acid 125 g of 2-chloro-4,5-difluoro-α,α-dichloroacetophenone from Example 6 are added dropwise at 30° C. and with stirring in the course of about 2 h to 1258 g of sodium hypobromite solution (prepared from 114 g of sodium hydroxide and 984 g of H$_2$O with the addition of 160 g of bromine at 0° C. to 10° C.). The mixture is subsequently stirred at 30° C. for 45 min and the at 50° C. for 3 h.

After separating off the organic phase, the aqueous phase is brought to pH 1 at about 40° C. using 140 of hydrochloric acid (32% strength) with the addition of sodium disulphite.

In this manner, 83 g of 2-chloro-4,5-difluorobenzoic acid are obtained, which corresponds to 86% of theory, relative to 1-chloro-3,4-difluorobenzene in Example 6.

Purity (from HPLO)=99%.

M.p.: 103° to 105° C.

EXAMPLE 8

2-Chloro-4,5-difluorobenzoic acid 125 g of 2-chloro-4,5-difluoro-α,α-dichloroacetophenone, prepared according to Example 6, are added dropwise at 60° C. with stirring in the course of 1.5 h to 1000 g of sodium hypochlorite solution (12% strength in NaOCl). The mixture is subsequently stirred at 60° C. for 30 min and heated to boiling for 2½ h, and the organic phase formed is separated off during the course of this by means of a liquid separator.

The aqueous phase is brought to pH 1 at about 40° C. using 80 ml of hydrochloric acid (32% strength) with the addition of sodium disulphite. After customary isolation and drying, 82 g of 2-chloro-4,5-difluorobenzoic acid are obtained, which corresponds to 85% of theory, relative to 1-chloro-3,4-difluorobenzene.

Purity (from HPLC)=99.3%

EXAMPLE 9

2,4,5-Trifluoro-α,α-dichloroacetophenone

A suspension of 66.1 g (0.5 mol) of 1,2,4-trifluorobenzene and 133.4 g (1 mol) of aluminium chloride is warmed to 55° C. 110 g (0.75 mol) of dichloroacetyl chloride are metered into this suspension at this temperature with the exclusion of moisture and with stirring in the course of 2 h. A continuous stream of HCl gas is evolved.

In order to complete the reaction, the mixture is allowed to react further at 60° C. for about 2 h. The evolution of HCl gas clearly subsides towards the end of the reaction. The liquid reaction mixture is poured into 1 l of water for hydrolysis. During the course of this, it is thoroughly stirred. After completion of the hydrolysis, the organic phase is separated off at 40° C..

116 g of the title compound are obtained without further intermediate purification, which corresponds to 95.5% of theory.

Purity (from GC/MS)=95%.

MS: Molar mass peak $M^+$=m/e 242 (244), $M^+$—CO—Cl—m/e 179, $M^+$—CHCl$_2$=m/e 159, $M^+$—(CHCl$_2$CO)=m/e 131.

$^{19}$F—NMR (CDCl$_3$) δ ppm, relative to C$_6$F$_6$: −22.4 ppm to −23.4 ppm (1 F, m), −40.4 ppm to −41.4 ppm (1 F, m), −53.7 ppm to −54.7 ppm (1 F, m).

EXAMPLE 10

2,4,5-Trifluorobenzoic acid 116 g of 2,4,5-trifluoro-α,α-dichloroacetophenone (from Example 9) are added dropwise at 30° C. with stirring in the course of about 2 h to 1258 g of sodium hypobromite solution (9.5% strength in NaOBr, corresponding to 1 mol). The mixture is subsequently stirring at 30° C. for 30 min and then at 50° C. for 3 h. After separating off the organic phase, the aqueous phase is diluted with 250 ml of water and brought to pH 1 using 145 ml of hydrochloric acid (32% strength ) at 40° C. with the addition of sodium disulphite.

In this manner, 72 g of 2,4,5-trifluorobenzoic acid are obtained, which corresponds to 82% of theory, relative to 1,2,4-trifluorobenzene in Example 9.

Purity (from HPLC)=99%.

M.p.: 96° to 98° C.

EXAMPLE 11

2-Bromo-4,5-difluoro-α, α-dichloroacetophenone 133.4 g (1 mol) of aluminium chloride are added at room temperature with stirring to 96.5 g (0.5 mol) of 3,4-difluorobromobenzene. The suspension is warmed to 70° C. and 110 g (0.75 mol) of dichloroacetyl chloride are added dropwise with the exclusion of moisture in the course of 2 h. In order to complete the reaction, the mixture is subsequently stirred at 70° C. for 1 h. After completion of the reaction, the liquid reaction mixture is poured into 1 l of water for hydrolysis. The mixture is well stirred during the course of this, and the temperature is allowed to rise to about 60° C. The organic phase is separated off at about 50° C.

151 g of 2-bromo-4,5-difluoro-α,α-dichloroacetophenone are obtained, which corresponds to 99% of theory.

Purity (from GC/MS)=80%. MS: Molar mass peak $M^+$=m/e 302/304, $M^+$—CO—Cl=m/e 239/241, $M^+$—$CHCl_2$=m/e 219 base peak/m/e 221, $M^+$—($CHCl_2CO$) =m/e 191/193.

$^{19}F$—NMR ($CDCl_3$) δ ppm, relative to $C_6F_6$: −25.8' ppm to −26.6 ppm (1 F, m), −33.5 ppm to −34.6 ppm (1 F, m).

EXAMPLE 12

2-Bromo-4,5-difluorobenzoic acid 151 g of 2-bromo-4,5-difluoro-α,α-dichloroacetophenone are added dropwise at 30° C. with stirring in the course of about 1 ¼ h to 1258 g of sodium hypobromite solution (9.5% strength in NaOBr corresponding to 1 mol). The mixture is subsequently stirred at 30° C. for 30 min and then at 50° C. for 3 h.

After separating off the organic phase, the aqueous phase is brought to pH 1 at about 40° C. using 125 ml of hydrochloric acid (32% strength) with the addition of sodium disulphite. After customary isolation, 101 g of 2-bromo-4,5-difluorobenzoic acid are obtained, which corresponds to 85% of theory, relative to 1-bromo-3,4-difluorobenzene in Example 11.

Purity (from HPLC)=94%.

Melting point m.p.: 108° to 110° C.

EXAMPLE 13

4-Chloro-2,5-difluoro-α,α-dichloroacetophenone and 74.3 g (0.5 mol) of 1-chloro-2,5-difluorobenzene and 133.4 g (1 mol) of aluminium chloride are brought to reaction at 65° C. according to Example 6. 89 g (0.6 mol) of dichloroacetyl chloride are added dropwise with the exclusion of moisture in the course of 3 h and the mixture is subsequently stirred at 70° C. for 2 h, so that the entire reaction time is 4.5 h. The mixture is hydrolysed in 1 l of water and the organic phase is separated off at 40° C. in a separating funnel. 124 g of liquid reaction product are obtained, which is 95% of theory, relative to 1-chloro-2,5-difluorobenzene.

Purity (from GC/MS)=93% MS: Molar mass peak $M^{30}$=m/e 258 (260), $M^+$—CO—Cl=m/e 195, $M^+$—$CHCl_2$=m/e 175 base peak, $M^+$—($CHCl_2CO$)=m/e 148.

$^{19}F$—NMR ($CDCl_3$) δ ppm, relative to $C_6F_6$: −43.7 ppm to −44.6 ppm (1 F, m), −50.6 ppm to −51.4 ppm (1F, m).

EXAMPLE 14

4-Chloro-2,5-difluoro-benzoic acid 124 g of 4-chloro-2,5-difluoro-α,α-dichloroacetophenone from Example 13 are added dropwise with stirring at 30° C. in the course of 1 h to 1258 g of sodium hypobromite solution (9.5% strength). The mixture is subsequently stirred at 30° C. for 45 min and then at 50° C. for 3 h.

After diluting with 1500 ml of water, the mixture is brought to pH 6 using 70 ml of hydrochloric acid (32% with the addition of sodium disulphite and the organic phase is separated off. The benzoic acid is then precipitated to pH 1 using 50 ml of hydrochloric acid (32%) with the addition of sodium disulphite. In this manner, 77.3 g of 4-chloro-2,5-difluorobenzoic acid are obtained, which corresponds to 80.3% of theory, relative to 0.5 mol of 1-chloro-2,5-difluorobenzene employed in Example 13.

Purity (from HPLC): 99.5%.

M.p.: 153° to 155° C.

EXAMPLE 15

3,4-Difluoro-α,α-dichloroacetophenone 57 g (0.5 mol) of 1,2-difluorobenzene and 93.4 g (0.7 mol) of aluminium chloride are brought to reaction with stirring at 30° C. and with the exclusion of moisture with 88.4 g (0.6 mol) of dichloroacetyl chloride. Including the metering-in time, the mixture is warmed at 30° C. for a total of 3 h. Towards the end of the reaction, the evolution of HCl clearly subsides. The reaction mixture is poured into 1 l of ice-water with stirring for hydrolysis. The liquid product is separated off at 25° C. in a separating funnel.

105 g of the title compound are obtained, which corresponds to 93% of theory, relative to 1,2-difluorobenzene.

Purity (from GC/MS)=96%.

MS: Molar mass peak $M^+$=m/e 224 (226) with $^{35}Cl$, $M^+$—CO—$^{35}Cl$=m/e 161, $M^+$—$CHCl_2$=m/e 141 base peak, $M^+$—($CHCl_2CO$)=m/e 113.

$^{19}F$—NMR ($CDCl_3$) δ ppm, relative to $C_6F_6$: −27.1 ppm to −28.1 ppm (1f, m), −35.4 ppm to −36.6 ppm (1 F, m).

EXAMPLE 16

3,4-Difluorobenzoic acid

The 3,4-difluoro-α,α-dichloroacetophenone obtained in Example 15 is oxidized with sodium hypobromite solution without intermediate purification according to the procedure in Example 10 to 3,4-difluorobenzoic acid.

68 g of the title compound are obtained, which corresponds to 86% of theory, relative to 1,2-difluorobenzene employed in Example 15.

Purity (from HPLC)=99%.

M.p.: 120° to 122° C.

EXAMPLE 17

2,5-Difluoro-α,α-dichloroacetophenone

A suspension of 57 g (0.5 mol) of 1,4-difluorobenzene and 93.4 g (0.7 mol of anhydrous aluminium trichloride is warmed to 45° C. At this temperature, 88.4 g (0.6 mol) of dichloroacetyl chloride is metered into the suspension with the exclusion of moisture and with stirring in the course of 2 h.

In order to complete the reaction, the mixture is subsequently allowed to react at 45° C. for 1 h. After completion of the reaction, the liquid reaction mixture is poured into 1 l of water for hydrolysis. The mixture is well stirred during the course of this and the temperature is allowed to rise to 40° C. The organic phase is separated off sharply at about 40° C. 96 g of 2,5-difluoro-α,α-dichloroacetophenone are obtained, which corresponds to 85.3% of theory, relative to 1,4-difluorobenzene employed.

Purity (from GC/MS): 93.5% (6.1% of 1,4-difluorobenzene).

MS: Molar mass peak $M^{30}=m/e$ 224 (226) with $^{35}Cl$, $M^+-CO-^{35}Cl=m/e$ 161, $M^+-CHCl_2=m/e$ 141 base peak, $M^+-(CHCl_2CO)=m/e$ 113.

$^{19}F$—NMR (CDCl$_3$) δ ppm, relative to C$_6$F$_6$: −45.7 ppm to −46.6 ppm (1 F, m), −48 ppm to −48.9 ppm (1 F, m).

EXAMPLE 18

2,5-Difluorobenzoic acid 96 g of 2,5-difluoro-α,α-dichloroacetophenone from Example 17 are added dropwise at 30° C. and with stirring in the course of about 1¼ h to 1258 g of sodium hypobromite solution (9.5% strength). The mixture is subsequently stirred at 30° C. for 45 min and then at 50° C. for 3 h.

After diluting with 250 ml of water, the mixture is brought to pH 6 using 75 ml of hydrochloric acid (32%) with the addition of sodium disulphite and the organic phase is separated off. It is then brought to pH 1 using 50 ml of hydrochloric acid (32%) with the addition of sodium disulphite.

63.6 g of 2,5-difluorobenzoic acid are obtained, which corresponds to 80.5% of theory, relative to 0.5 mol of 1,4-difluorobenzene employed in Example 17.

Purity (from HPLC): 99.6%.

Melting point m.p.: 128° to 130° C.

I claim:

1. Fluorinated chloroacetophenone of the formula II

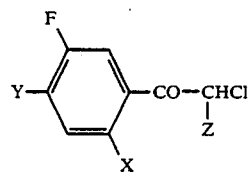

in which
Z denotes Cl and
X denotes Br, Cl, F or H
Y denotes Cl, F or H and
wherein at least one of the radicals X or Y is not hydrogen.

2. Fluorinated chloroacetophenones according to claim 2, characterized in that Y denotes fluorine and X denotes fluorine or chlorine.

3. Process for the preparation of a fluorinated chloroacetophenone of the formula II

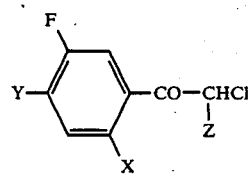

in which
Z denotes Cl and
X denotes Br, Cl, F or H and
Y denotes Cl, F or H and
wherein at least one of the radical X or Y is not hydrogen,
characterized in that the compound of formula (II) is prepared by reacting a compound of the formula III

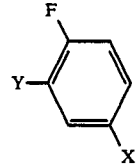

in which
X denotes Br, Cl, F or H
Y denotes Cl, F or H
wherein at least one of the radicals X or Y is not hydrogen
with dichloroacetyl chloride in the presence of an acylating catalyst.

4. Process according to claim 2, characterized in that the reaction is carried out at a temperature of 20° to 100° C.

5. Process according to claim 2, characterized in that the reaction is carried out at a temperature of 20° C. to 90° C.

6. Process according to claim 2, characterized in that a compound of the formula III is reacted with dichloroacetyl chloride at a temperature of 20° to 70° C.

* * * * *

UNITED STATES PATENT AND TRADEMARK OFFICE
CERTIFICATE OF CORRECTION

PATENT NO. : 5,093,529

DATED : March 3, 1992

INVENTOR(S) : Horst Schmand

It is certified that error appears in the above-identified patent and that said Letters Patent is hereby corrected as shown below:

In column 1, line 43, the phrase "if the liberation" should read --is the liberation--.

In column 1, line 52, the phrase "is then reacted" should read --is then extracted--.

In column 2, line 49 should read --X denotes Br, Cl or F,--.

In column 3, line 23, the word "hypohalide" should read --hypohalite--.

In column 4, line 19, the phrase "dichloroacetyl chlorine" should read --dichloroacetyl chloride--.

In column 4, line 35, the word "trichlorethane" should read --trichloroethane--.

In column 4, line 54, the phrase "cases : (1.1 to 1.6):(1.3 to 2.1)" should read --cases 1:(1.1 to 1.6):(1.3 to 2.1)--.

In column 5, line 53, the phrase "NRM spectra" should read --NMR spectra--.

In column 5, line 59, "(179 mol)" should read --(1.79 mol)--.

In column 6, line 13, "ppn" should read --ppm--.

UNITED STATES PATENT AND TRADEMARK OFFICE
CERTIFICATE OF CORRECTION

PATENT NO. : 5,093,529

DATED : March 3, 1992

INVENTOR(S) : Horst Schmand

It is certified that error appears in the above-identified patent and that said Letters Patent is hereby corrected as shown below:

In column 6, line 16, "F-NRM" should read --$^{19}$F-NMR--.

In column 6, line 26, the phrase "of 2 to 846 g" should read --of 2 h to 846 g--.

In column 6, line 30, the phrase "colourless aqueous" should read --colourless aqueous phase--.

In column 6, line 35, the word "trifulorobenzene" should read --trifluorobenzene--.

In column 6, line 52, "(C=O)" should read --(>C=O)--.

In column 7, line 27, "$M^{30}$" should read --$M^+$--.

In column 7, line 30, the word "-chloroacetopheone" should read -- --chloroacetophenone--.

In column 7, line 53, the phrase "$M^{30}$ = 258 m/e (260" should read --$M^+$ = m/e 258 (260)--.

In column 7, line 54, "$M^{30}$" should read --$M^+$--.

In column 8, line 1, the phrase "and the at" should read --and then at--.

UNITED STATES PATENT AND TRADEMARK OFFICE
CERTIFICATE OF CORRECTION

PATENT NO. : 5,093,529

DATED : March 3, 1992

INVENTOR(S) : Horst Schmand

It is certified that error appears in the above-identified patent and that said Letters Patent is hereby corrected as shown below:

In column 8, line 4, the phrase "using 140 of" should read --using 140 ml of--.

In column 8, line 10, "HPLO" should read --HPLC--.

In column 8, line 53, "$M^+-CO-Cl-m/e$" should read -- $M^+-CO-Cl=m/e$ --.

In column 8, line 66, the word "stirring" should read --stirred--.

In column 9, line 31, "$(CDCl)_3$" should read --$(CDCl_3)$--.

In column 9, line 32, "34.6 ppm" should read --34.5 ppm--.

In column 9, line 51, "110°C" should read --111°C--.

In column 9, line 68, "$M^{30}$" should read --$M^+$--.

UNITED STATES PATENT AND TRADEMARK OFFICE
CERTIFICATE OF CORRECTION

PATENT NO. : 5,093,529
DATED : March 3, 1992
INVENTOR(S) : Horst Schmand

It is certified that error appears in the above-identified patent and that said Letters Patent is hereby corrected as shown below:

In column 10, lines 1 and 2, "$M^+ —(CHCl\text{-}_2CO)$" should read --$M^+ —(CHCl_2\text{-}CO)$--.

In column 10, line 17, "(32%" should read --(32%)--.

In column 10, line 52, "(1f, m)" should read --(1F, m)--.

In column 11, line 6, "(0.7 mol" should read --(0.7 mol)--.

In column 11, line 27, "$M^{30}$" should read --$M^+$--.

Signed and Sealed this

Twenty-first Day of September, 1993

Attest:

BRUCE LEHMAN

*Attesting Officer*  *Commissioner of Patents and Trademarks*